United States Patent

Vogt et al.

[11] Patent Number: 6,071,857
[45] Date of Patent: Jun. 6, 2000

[54] PESTICIDAL COMPOSITIONS

[75] Inventors: Manfred Vogt, Bad Säckingen, Germany; William Baettig, Pratteln, Switzerland

[73] Assignee: Novartis Crop Protection, Inc., Greensboro, N.C.

[21] Appl. No.: 09/202,886
[22] PCT Filed: Jun. 19, 1997
[86] PCT No.: PCT/EP97/03195
   § 371 Date: Dec. 22, 1998
   § 102(e) Date: Dec. 22, 1998
[87] PCT Pub. No.: WO98/00009
   PCT Pub. Date: Jan. 8, 1998

[30] Foreign Application Priority Data

Jun. 28, 1996 [DE] Germany .......................... 968 10 432

[51] Int. Cl.$^7$ .............................. A01N 3/02; A01N 25/00
[52] U.S. Cl. ........................................... 504/116; 424/405
[58] Field of Search .............................. 504/116; 424/405

[56] References Cited

U.S. PATENT DOCUMENTS

| 4,870,103 | 9/1989 | Roechling et al. ...................... 514/521 |
| 4,973,352 | 11/1990 | Heinrich et al. ........................... 71/91 |

FOREIGN PATENT DOCUMENTS

| 299961 | 1/1989 | European Pat. Off. . |
| 2577533 | 1/1994 | European Pat. Off. . |
| 3640267 | 6/1988 | Germany . |
| 90/4202 | 6/1990 | Germany . |
| 4239181 | 5/1994 | Germany . |
| 92/6941 | 9/1992 | South Africa . |

*Primary Examiner*—José G. Dees
*Assistant Examiner*—Alton Pryor
*Attorney, Agent, or Firm*—William A. Teoli, Jr.; John D. Peabody, III; Irving M. Fishman

[57] ABSTRACT

A liquid pesticidal composition, which is substantially free of water, comprising a hydrophobic pesticide or mixture of pesticides dissolved in an organic solvent and comprising as surfactants (1) a butanol-ethoxyate/propoxylate-blockcopolymer having 12–30 mol ethoxylate and 16–48 mol propoxylate, in combination with (2) a branched $C_8$–$C_{18}$ alcohol ethoxylate having 5–10 mol ethoxylate, and/or (3) a tristyrenephenol-ethoxylate having 8–30 mol ethoxylate, or its phosphate or salt thereof.

The compositions include also gels having a viscosity of 500 to 20,000 mPas and comprising additionally a gelling agent.

38 Claims, No Drawings

PESTICIDAL COMPOSITIONS

This appln is a 371 of PCT/EP97/03195 filed Jun. 19, 1997.

The present invention relates to storage stable, liquid, pesticidal compositions, the preparation of such compositions and a method of using such compositions to combat pests or as plant growth regulators.

Alkylphenol ethoxylates, for example nonylphenol ethoxylates, and alkylbenzene sulfonates and its salts, for example dodecylbenzene sulfonate calcium salt, are commonly used and well known surfactants in water-emulsifiable pesticidal compositions.

Some of these surfactants are not entirely satisfactory; in particular with respect to their ecological and toxicological properties.

There is still a need for further water-emulsifiable or water soluble, liquid, homogeneous pesticidal compositions which are storage stable, ecological and toxicological favourable and which have good pesticidal efficacy.

Fatty alcohol ethoxylates, e.g. $C_{10}$–$C_{14}$ alcohol ethoxylates (EP-A-400,585) and tristyrenephenol-ethoxylates (EP-A-102,003) have been proposed, both in combination with alkylbenzene sulfonates, as surfactants in water-emulsifiable pesticidal compositions. $C_1$–$C_{10}$ Alkyl ethoxylate/propoxylate-blockcopolymers and tristyrenephenol-ethoxylates have been disclosed as surfactants in aqueous suspensions (EP-A-261,492).

A novel combination of surfactants for water-emulsifiable or water-soluble pesticidal compositions has now been found; the novel compositions are storage stable, easy to apply, ecological and toxicological favourable and have good pesticidal efficacy.

Accordingly, the present invention provides a water-emulsifiable or water-soluble, storage stable, liquid, pesticidal composition, which is substantially free of water, comprising a hydrophobic pesticide or mixture of pesticides dissolved in an organic solvent and comprising as surfactants (1) a butanol-ethoxylate/propoxylate-blockcopolymer having 12–30 mol ethoxylate and 16–48 mol propoxylate, in combination with (2) a branched $C_8$–$C_{18}$ alcohol ethoxylate having 5–10 mol ethoxylate, and/or (3) a tristyrenephenol-ethoxylate having 8–30 mol ethoxylate, or its phosphate or salt thereof.

Suitable salts with bases are, for example, metal salts, such as alkali metal or alkaline earth metal salts, for example sodium, potassium calcium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propylamine, or a mono-, di- or tri-hydroxy-lower alkylamine, for example mono-, di- or tri-ethanolamine.

The compositions also include gels having a viscosity of 500 to 20,000 mPas and comprising additionally a gelling agent.

The compositions according to the invention are stable for at least 12 months at 25° C. They are very well miscible with water, even at higher concentrations.

The surfactants can be combined, depending for example on the kind of pesticide and the preferred solvents, as follows:

(1) in combination with (2) and (3); (1) in combination with (2); (1) in combination with (3).

The surfactants mentioned above can be prepared by methods known per se; they are also commercially available.

Preferred are surfactants, wherein (1) the butanol-ethoxylate/propoxylate-blockcopolymer has 20–24 mol, preferably 22 mol ethoxylate, and 30–36 mol, most preferably 34 mol propoxylate;

(2) the branched $C_8$–$C_{18}$ alcohol ethoxylate is isotridecanol ethoxylate having 5–10 mol, most preferably 6–8 mol ethoxylate; and (3) the tristyrenephenol-ethoxylate has 16–18 mol ethoxylate.

The composition of the invention is substantially free of water, i.e. the amount of water is less that 0.5%. Some commercially available materials may contain a small amount of water, which, when more than about 0.1% can be removed for example in a separator.

In another aspect of the invention the composition is a gel with a viscosity of 500–20,000 mPas; preferably 800 to 10,000 mPas and particularly 1000–5000 mPas.

The viscosity of the composition can be measured using for example a BROOKFIELD viscosimeter with spindles 1 to 3 at 30 rpm.

In this case the composition additionally has to contain a gelling agent, for example oxypropylated cellulose, precipitated or fused silica (hydrophobizised or non-hydrophobizised), gelatine, polysaccharides, tetramethyl decyne diol, ethoxylated dialkyl phenol, methylated clay, propylene carbonate, hydrogenated castor oil, ethoxylated vegetable oil, sodium benzoate and hexanediol. Preferred gelling agent is oxypropylated cellulose.

Gels are particularly suitable for pesticides packing into water soluble bags or sachets, which quickly dissolve when put into the water.

The organic solvents wherein the pesticide has to be dissolved may be water-immiscible or water miscible or a mixture thereof.

Suitable water-immiscible solvents in which the pesticides may be dissolved are aliphatic and aromatic hydrocarbons such as hexane, cyclohexane, benzene, toluene, xylene, mineral oil or kerosin, mixtures or substituted naphthalenes, mixtures of mono- and polyalkylated aromatics commercially available under the registered trademarks SOLVESSO and SHELLSOL and PETROL SPEZIAL, halogenated hydrocarbons such as methylene chloride, chloroform and o-dichlorobenzene; phthalates, such as dibutyl phthalate or dioctyl phthalate; ethers and esters, such as ethylene glycol monomethyl or monoethyl ether, fatty acid esters; lactones such as butyrolactone, ketones, such as cyclohexanone; plant oils such as castor oil, soybean oil, cottonseed oil and possible methyl esters thereof; as well as epoxidised coconut oil or soybean oil. Preferred water-immiscible solvents are aliphatic and aromatic hydrocarbons, fatty acid esters (e.g. WITCONOL 2309), dipropyleneglycol monomethylether (e.g. DOWANOL DPM) and castor oil.

Suitable water-miscible solvents in which the pesticides may be dissolved are alcohols and glycols, such as ethanol, ethylene glycol, strongly polar solvents, such as N-methyl-2-pyrrolidone, tetramethylurea, gamma-butyrolacone, dimethyl sulfoxide, N,N-dimethylacetamid and dimethylformamide; preferred are N-methyl-2-pyrrolidone and gamma-butyrolacone.

Suitable pesticides are those which are substantially insoluble in water (hydrophobic), but soluble in the organic solvent.

The term pesticide is understood to encompass herbicides, insecticides, acaricides, nematicides, ectoparasiticides, fungicides and plant growth regulators.

With respect to their chemical constitution, these pesticides may belong to a very wide range of compound classes.

Examples of compound classes to which the suitable pesticide may belong are: acylalanines, haloacetanilides, triazole derivatives, phosphoric acid esters, pyrethroids, benzilic acid esters, polycyclic halogenated hydrocarbons, diphenyl ether derivates, formamidines, strobilurines, aryloxyphenoxy-alkanoic acid derivatives. Examples of suitable individual compounds of the above mentioned compound classes are listed below. Where known, the common name is used to designate the individual compounds (q.v. the Pesticide Manual, 10th edition, 1994, British Crop Protection Council).

Haloacetanilides: Dimethachlor, Metolachlor, Pretilachlor, 2-chloro-N-(1-methyl-2-methoxyethyl)-acet-2,6-xylidide, Alachlor, Butachlor, Propachlor, Dimethenamid.

Diphenyl ether derivates: Bifenox, 4-(4-Pentyn-1-yloxy) diphenylether, Acifluorfen, Oxyfluorfen, Fluoroglycofen-ethyl, Fomesafen, cis-trans-(±)2-ethyl-5-(4-phenoxy-phenoxymethyl)-1,3-dioxolane ("diofenolan").

Phenoxypropionic acid derivatives: Fluazifop-butyl, Haloxyfop-methyl, Haloxyfop-(2-ethoxyethyl), Fluorotopic, Fenoxapropethyl, Quizalofop-ethyl, Propaquizafop, Diclofop-methyl.

Acylalanines: Furalaxyl, Metalaxyl, R- Metalaxyl, Benzoylprop ethyl, Benalaxyl, Oxadixyl, Flamprop methyl.

Triazole derivatives: Difenoconazole, Etaconazol, Propiconazole, Penconazole, Triadimefon, Epoxiconazole, Tebuconazole, Bromuconazole, Fenbuconazole, Cyproconazole.

Phosphoric acid esters: Piperophos, Anilofos, Butamifos, Azamethiphos, Chlorfenvinphos, Dichlorvos, Diazinon, Methidathion, Azinphos ethyl, Azinphos methyl, Chlorpyrifos, Chlorthiofos, Crotoxyphos, Cyanophos, Demeton, Dialifos, Dimethoate, Disulfoton, Etrimfos, Famphur, Flusulfothion, Fluthion, Fonofos, Formothion, Heptenophos, lsofenphos, Isoxathion, Malathion, Mephospholan, Mevinphos, Naled, Oxydemeton methyl, Oxydeprofos, Parathion, Phoxim, Pyrimiphos methyl, Profenofos, Propaphos, Propetamphos, Prothiophos, Quinalphos, Sulprofos, Phemephos, Terbufos, Triazophos, Trichloronate, Fenamipos, Isazophos, s-benzyl-o,o-diisopropylphosphorothioate, Edinphos, Pyrazophos.

Pyrethroids: Allethrin, Bioallethrin, Bioresmethrin, Cyhalotrin, Cypermethrin, α-Cypermethrin, φ-Cypermethrin, Deltamethrin, Fenpropathrin, Fenvalerate, s-Fenvalerate, Flucythrinate, Fluvalinate, Permethrin, Pyrethrine, Resmethrin, Tetramethrin, Tralomethrin, Ethophenprox, Cyfluthrin, Cycloprothrin, Tefluthrin, Flufenprox, Silafluofen, Bifenthrin, Fenfluthrin, Bromfenprox.

Benzilic acid esters: Brompropylate, Chlorbenzylate, Chlorpropylate.

Polycyclic haloaenated hydrocarbons: Aldrin, Endosulfan.

Strobilurines: Kresoxim-methyl, Azoxystrobin (BAS 490F), Methoxyimino-{2-[1-(3-trifluoromethyl-phenyl)-ethylideneaminooxymethyl]-phenyl}-acetic acid methyl ester.

Miscellaneous: Tridemorph, Bromoxynil, Carboxin, Prochloraz, Propargite, Dicamba, Fenpiclonil, Fenpropimorph, Fenpropidin, Fludioxonil, Pymetrozine, Pyrifenox, Pyriproxyfen, Trinexapac-ethyl, Fluazinam.

Preferred pesticides are herbicides, as Propaquizafop, Piperophos and Propanil;

fungicides, as Methoxyimino-{2-[1-(3-trifluoromethyl-phenyl)- ethylideneaminooxymethyl]-phenyl}-acetic acid methyl ester, Propiconazole, Cyproconazole, Fluazinam, Metalaxyl or R-Metalaxyl (enantiomer of Metalaxyl), or a mixture thereof;

insecticides, as Diazinon;

plant growth regulators, as Trinexapac-ethyl.

Suitable concentrations in relation to the composition are (% weight per volume of the total composition; 1000 g per liter correspond to 100%)

a) of the hydrophobic pesticide or mixture of pesticides: 1 to 99%, preferably 10 to 90% and 20 to 50%;

b) of the organic solvent: 1 to 96%, preferably 10 to 80% and 20 to 70%;

c) of the surfactants: 3 to 80%, preferably 10 to 40% and 20 to 30%; wherein of surfactant (1): 2 to 25%, preferably 5 to 20%,
surfactant (2): 2 to 40%, preferably 5 to 25%,
surfactant (3): 2 to 20%, preferably 5 to 15%;

d) of the gelling agent: 0.1 to 10 % preferably 0.5 to 5%.

It may be advantageous to add additionally an alkylbenzene sulfonate or its salt, preferably dodecylbenzene sulfonate calcium salt in an amount of 1 to 10%, preferably 2 to 4 % by weight in relation to the volume of the composition.

It may be advantageous to combine the pesticide or mixture of pesticides with a safener.

Another object of the invention is a process for preparing a liquid pesticidal composition as herein described, by intimateley mixing, optionally by warming, until a homogeneous phase is achieved.

In another aspect of the invention the composition is an aqueous spray mixture.

Before the application, the composition of the invention may be diluted with water by simple mixing at ambient temperature in order to get a ready for use spray mixture.

This spray mixture may be an aqueous emulsion or a solution or a suspension, depending on the kind of composition.

The resulting spray mixtures are stable, i.e. they remain as a homogeneously emulsified phase, as a solution or as a homogeneously distributed suspension on standing without agitation for at least one hour to 12 hours or even more.

Preferred concentrations of the spray mixture are 0.1 to 5 %, more preferred 0.5 to 2% pesticide in relation to the spray mixture.

Further aspects of the invention include a method of preventing or combatting infestation of plants or animals by pests and regulating plant growth by diluting the composition with water and applying a pesticidally effective amount to the plant, animal or locus as desired.

PREPARATION EXAMPLES

The following Examples illustrate the invention in more detail. The registered trademarks and other designations denote the following products:

| | | |
|---|---|---|
| (1) WITCONOL NS 500 K ® (WITCO) | | Copolymer of butanol-34 PO/22 EO, |
| (2) GENAPOL X-080 ® (HOECHST) | | Isotridecanol-8 EO |
| GENAPOL X-060 ® (HOECHST) | | Isotridecanol-6 EO |

-continued

| | | |
|---|---|---|
| (3) SPROPHOR BSU ® (RHÔNE-P) | Tristyrenephenole-16 EO | |
| SOPROPHOR 3D33 ® (RHÔNE-P) | Tristyrenephenol-poly-EO-phosphate | |

WITCONOL 2309 ® Fatty acid methylester
EMULSOGEN EL ® castor oil-36 EO
SPEZIAL 200 ® Mixture of aromatic hydrocarbons
KLUCEL M ® Oxypropylated cellulose (gelling agent)
DOWANOL DPM ® Dipropyleneglcyol monomethylether (mixture of isomers)
EO = ethyleneoxid
PO = propyleneoxid % in weight per volume of the total composition (i.e.1000 g per liter correspond to 100%). The components are intimateley mixed, optionally by warming, until a homogeneous phase is achieved.

Example 1

| % | component | type |
|---|---|---|
| 10.0 | Propaquizafop | herbicide |
| 5.0 | WITCONOL NS 500 K ® | surfactant (1) |
| 35.0 | GENAPOL X-060 ® | surfactant (2) |
| 10.0 | 1-Methyl-2-pyrrolidone | solvent |
| 40.0 | PETROL SPEZIAL 200 | solvent |

Density: 1.02 g/cm$^3$

Example 2

| % | component | type |
|---|---|---|
| 14.5 | Piperophos | herbicide |
| 25.0 | Propanil | herbicide |
| 8.0 | WITCONOL NS 500 K ® | surfactant (1) |
| 12.0 | GENAPOL X-060 ® | surfactant (2) |
| 40.5 | Dipropyleneglycol monomethyl ether | solvent |

Density: 1.065 g/cm$^3$

Example 3

| % | component | type |
|---|---|---|
| 17.4 | Methoxyimino-{2-[1-(3-trifluoromethyl-phenyl)-ethylidene-aminooxymethyl]-phenyl}-acetic acid methyl ester | fungicide |
| 12.3 | Propiconazole | fungicide |
| 11.7 | WITCONOL NS 500 K ® | surfactant (1) |
| 11.7 | SOPROPHOR BSU ® | surfactant (3) |
| 46.9 | 1-Methyl-2-pyrrolidone | solvent |

Density: 1.11 g/cm$^3$

Example 4

| % | component | type |
|---|---|---|
| 12.1 | Methoxyimino-{2-[1-(3-trifluoromethyl-phenyl)-ethylidene-aminooxymethyl]-phenyl}-acetic acid methyl ester | fungicide |
| 11.7 | WITCONOL NS 500 K ® | surfactant (1) |
| 9.3 | SOPROPHOR BSU ® | surfactant (3) |
| 2.3 | SOPROPHOR 3D33 ® | surfactant (3) |
| 64.6 | 1-Methyl-2-pyrrolidone | solvent |

Density: 1.07 g/cm$^3$

Example 5

| % | component | type |
|---|---|---|
| 11.8 | Methoxyimino-{2-[1-(3-trifluoromethyl-phenyl)-ethylidene-aminooxymethyl]-phenyl}-acetic acid methyl ester | fungicide |
| 12.5 | Propiconazole | fungicide |
| 11.4 | WITCONOL NS 500 K ® | surfactant (1) |
| 11.4 | SOPROPHOR BSU ® | surfactant (3) |
| 52.9 | 1-Methyl-2-pyrrolidone | solvent |

Density: 1.095 g/cm$^3$

Example 6

| % | component | type |
|---|---|---|
| 19.0 | Methoxyimino-{2-[1-(3-trifluoromethyl-phenyl)-ethylidene-aminooxymethyl]-phenyl}-acetic acid methyl ester | fungicide |
| 12.5 | Propiconazole | fungicide |
| 13.0 | WITCONOL NS 500 K ® | surfactant (1) |
| 10.0 | SOPROPHOR BSU ® | surfactant (3) |
| 3.0 | SOPROPHOR 3D33 ® | surfactant (3) |
| 42.5 | 1-Methyl-2-pyrrolidone | solvent |

Density: 1.1 g/cm$^3$

Example 7

| % | component | type |
|---|---|---|
| 23.3 | Cyproconazole | fungicide |
| 10.0 | WITCONOL NS 500 K ® | surfactant (1) |
| 10.0 | SOPROPHOR 3D33 ® | surfactant (3) |
| 23.0 | 1-Methyl-2-pyrrolidone | solvent |
| 33.7 | SOLVESSO 200 | solvent |

Density: 1.073 g/cm$^3$

Example 8

| % | component | type |
|---|---|---|
| 12.5 | Methoxyimino-{2-[1-(3-trifluoromethyl-phenyl)-ethylidene-aminooxymethyl]-phenyl}-acetic acid methyl ester | fungicide |
| 12.5 | WITCONOL NS 500 K ® | surfactant (1) |
| 10.0 | SOPROPHOR BSU ® | surfactant (3) |
| 2.5 | SOPROPHOR 3D33 ® | surfactant (3) |
| 62.5 | 1-Methyl-2-pyrrolidone | solvent |

Density: 1.07 g/cm$^3$

Example 9

| % | component | type |
|---|---|---|
| 18.5 | Methoxyimino-{2-[1-(3-trifluoromethyl-phenyl)-ethylidene-aminooxymethyl]-phenyl}-acetic acid methyl ester | fungicide |
| 8.0 | Cyproconazole | fungicide |
| 10.0 | WITCONOL NS 500 K | surfactant (1) |
| 5.0 | GENAPOL X-080 ® | surfactant (2) |
| 5.0 | SOPROPHOR BSU ® | surfactant (3) |
| 53.5 | 1-Methyl-2-pyrrolidone | solvent |

Density: 1.09 g/cm$^3$

Example 10

| % | component | type |
|---|---|---|
| 15.0 | Methoxyimino-{2-[1-(3-trifluoromethyl-phenyl)-ethylidene-aminooxymethyl]-phenyl}-acetic acid methyl ester | fungicide |
| 7.0 | R-Metalaxyl | fungicide |
| 12.5 | WITCONOL NS 500 K | surfactant (1) |
| 12.5 | SOPROPHOR BSU ® | surfactant (3) |
| 53.0 | 1-Methyl-2-pyrrolidone | solvent |

Density: 1.081 g/cm$^3$

Example 11

| % | component | type |
|---|---|---|
| 12.5 | Methoxyimino-{2-[1-(3-trifluoromethyl-phenyl)-ethylidene-aminooxymethyl]-phenyl}-acetic acid methyl ester | fungicide |
| 7.5 | R-Metalaxyl | fungicide |
| 3.0 | WITCONOL NS 500 K | surfactant (1) |
| 3.0 | GENAPOL X-080 ® | surfactant (2) |
| 45.5 | 1-Methyl-2-pyrrolidone | solvent |
| 27.5 | Aromatic solvent 230 | solvent |

Density: 1.081 g/cm$^3$

Example 12

| % | component | type |
|---|---|---|
| 9.3 | R-Metalaxyl | fungicide |
| 4.0 | WITCONOL NS 500 K | surfactant (1) |
| 16.0 | GENAPOL X-080 ® | surfactant (2) |
| 5.0 | Gamma-Butyrolactone | solvent |
| 27.0 | Fatty acid methyl ester Me C 6-10 | solvent |

Density: 1.035 g/cm$^3$

Example 13

| % | component | type |
|---|---|---|
| 17.7 | R-Metalaxyl | fungicide |
| 26.0 g | Fluazinam | fungicide |
| 5.0 | WITCONOL NS 500 K | surfactant (1) |
| 5.0 | GENAPOL X-060 ® | surfactant (2) |
| 5.0 | SOPROPHOR BSU ® | surfactant (3) |
| 16.0 | PETROL SPEZIAL 200 ® | solvent |
| 25.3 | Gamma-Butyrolactone | solvent |

Density: 1.184 g/cm$^3$

Example 14

| % | component | type |
|---|---|---|
| 59.6 | Diazinon | insecticide |
| 8.0 | WITCONOL NS 500 K ® | surfactant (1) |
| 8.0 | SOPROPHOR BSU ® | surfactant (3) |
| 24.4 | SOLVESSO 150 | solvent |

Density: 1.073 g/cm$^3$

Example 15

| % | component | type |
|---|---|---|
| 26 | Trinexapac-ethyl | plant growth regulator |
| 21.0 | WITCONOL NS 500 K | surfactant (1) |
| 7.0 | GENAPOL X-060 ® | surfactant (2) |
| 0.8 | KLUCEL M ® | gelling agent |
| 45.2 | DOWANOL DPM ® | solvent |

Density: 1.027 g/cm$^3$; Viscosity; ca. 2700 mPas (Spindle 3/30 rpm)

Example 16

| % | component | type |
|---|---|---|
| 26.3 | Trinexapac-ethyl | plant growth regulator |
| 21.4 | WITCONOL NS 500 K | surfactant (1) |
| 7.1 | GENAPOL X-060 ® | surfactant (2) |
| 45.2 | WITCONOL 2309 ® | solvent |

Density: 0.98 g/cm$^3$

All the compositions according to the examples are stable for at least 12 months at 25° C.

After diluting with water the compositions form an emulsion or, depending on the pesticide, solvent and concentration, a clear solution. Both the emulsions and solutions are stable without agitation for at least one to 12 hours or even more.

What is claimed is:

1. A liquid pesticidal composition comprising a hydrophobic pesticide or mixture of pesticides dissolved in an organic solvent together with surfactants, which composition is substantially free of water and comprising as said surfactants (1) a butanol-ethoxylate/propoxylate blockcopolymer having 12–30 mol ethoxylate and 16–48 mol propoxylate, in combination with (2) a branched $C_8$–$C_{18}$ alcohol ethoxylate having 5–10 mol ethoxylate, and/or (3) a tristyrenephenol-ethoxylate having 8–30 mol ethoxylate, or its phosphate or salt thereof;

wherein said organic solvent is water-immiscible and selected from the group consisting of aliphatic and aromatic hydrocarbons, phthalates, ethers and esters, fatty acid esters, lactones, ketones, castor oil, soybean oil, cottonseed oil and possible methyl esters thereof, and epoxidised coconut or soybean oil or wherein said organic solvent is water miscible and selected from the group consisting of alcohols, glycols N-methyl-2-pyrrolidone, tetramethylurea, gamma-butyrolactone, dimethylsuloxide N,N-dimethylacetamid, and dimethylformamide;

whereby a storage stable composition is obtained.

2. A composition according to claim 1, wherein the butanol-ethoxylate/propoxylate-blockcopolymer (1) has 20–24 mol ethoxylate, and 30–36 mol propoxylate.

3. A composition according to claim 1, wherein the branched $C_8$–$C_{18}$ alcohol ethoxylate (2) is isotridecanol ethoxylate having 5–10 mol ethoxylate.

4. A composition according to claim 1, wherein the tristyrenephenol-ethoxylate (3) has 16–18 mol ethoxylate.

5. A composition according to claim 1 having a viscosity of 800 to 10,000 mPas.

6. A composition according to claim 5, wherein the gelling agent is selected from the group consisting of oxypropylated cellulose, precipitated or fused silica gelatine, polysaccharides, tetramethyl decyne diol, ethoxylated dialkyl phenol, methylated clay, propylene carbonate, hydrogenated castor oil, ethoxylated vegetable oil, sodium benzoate and hexanediol.

7. A composition according to claim 6, wherein the gelling agent is oxypropylated cellulose.

8. A composition according to claim 1, wherein the surfactants are (1) a butanol-ethoxylate/propoxylate-blockcopolymer having 12–30 mol ethoxylate and 16–48 mol propoxylate, in combination with (2) a branched $C_8$–$C_{18}$ alcohol ethoxylate having 5–10 mol ethoxylate.

9. A composition according to claim 1, wherein the surfactants are (1) a butanol-ethoxylate/propoxylate-blockcopolymer having 12–30 mol ethoxylate and 16–48 mol propoxylate, in combination with (3) a tristyrenephenol-ethoxylate having 8–30 mol ethoxylate, or its phosphate or salt thereof.

10. A composition according to claim 1, wherein the organic solvent is selected from aliphatic and aromatic hydrocarbons, fatty acid esters, dipropyleneglycol monomethylether and castor oil.

11. A composition according to claim 1, wherein the organic solvent is N-methyl-2-pyrrolidone or gamma-butyrolacone or a mixture thereof.

12. A composition according to claim 1, wherein the pesticide is a herbicide.

13. A composition according to claim 1, wherein the pesticide is a fungicide.

14. A composition according to claim 1, wherein the pesticide is an insecticide.

15. A composition according to claim 1, wherein the pesticide is a plant growth regulator.

16. A composition according to claim 1, wherein the concentration of the pesticide or mixture of pesticides is 1 to 99% by weight in relation to the volume of the composition.

17. A composition according to claim 16, wherein the concentration of the pesticide or mixture of pesticides is 10 to 90% in relation to the volume of the composition.

18. A composition according to claim 1, wherein the concentration of the organic solvent is 1 to 96% by weight in relation to the volume of the composition.

19. A composition according to claim 18, wherein the concentration of the organic solvent is 10 to 80% by weight in relation to the volume of the composition.

20. A composition according to claim 1, wherein the concentration of the surfactants (1), (2) and/or (3) is 3 to 80% by weight in relation to the volume of the composition.

21. A composition according to claim 20, wherein the concentration of the surfactants is 10 to 40% by weight in relation to the volume of the composition.

22. A process for preparing a liquid pesticidal composition according to claim 1 by intimately mixing, optionally by warming, said pesticide, said organic solvent, and said surfactants until a homogeneous phase is obtained.

23. An aqueous microemulsion or solution prepared by mixing the composition according to claim 1 with water.

24. A method of preventing or combatting infestation of plants or animals by pests by diluting the composition according to claim 1 with water and applying a pesticidally effective amount to the plant, animal or locus.

25. The composition of claim 2 wherein said butanol-ethoxylate/propoxylate-blockcopolymer (1) has 22 mol ethoxylate and 34 mol propoxylate.

26. The composition of claim 3 wherein the branched $C_8$–$C_{18}$ alcoholethoxylate is isotridecanol ethoxylate having 6–8 mol ethoxylate.

27. The composition of claim 5 having a viscosity of 1000–5000 mPas.

28. The composition of claim 12 wherein said pesticide is a herbicide and is selected from the group consisting of Propaquizafop, Piperaphos, and Propanil.

29. The composition of claim 13 wherein said pesticide is a fungicide and is selected from the group consisting of methoxyimino-{2-[-(-trifluoromethyl-phenyl)-ethylideneaminooxymethyl]-phenyl} acetic acid methyl ester, Propiconazole, Cyproconazole, fluazinam, Metalaxyl or R-Metalaxyl, and mixtures thereof.

30. The composition of claim 14 wherein said pesticide is Diazinon.

31. The composition of claim 15 wherein said pesticide is Trinexapac-ethyl.

32. The composition of claim 17 wherein said pesticide is present in said composition at a concentration of 20 to 50% in relation to the volume of the composition.

33. The composition of claim 19 wherein said organic solvent is present in said composition at a concentration of 20 to 70% in relation to the volume of the composition.

34. The composition of claim 21 wherein said surfactants are present in said composition at a concentration of 20 to 30% in relation to the volume of the composition.

35. The method of claim 24 which further regulates plant growth wherein said pesticide is a plant growth regulator and said composition is applied to said plant or locus.

36. A liquid pesticidal composition, which is substantially free of water, comprising a hydrophobic pesticide or mixture of pesticides dissolved in an organic solvent and comprising as surfactants (1) a butanol-ethoxylate/propoxylate blockcopolymer having 12–30 mol ethoxylate and 16–48 mol propoxylate, in combination with (2) a branched $C_8$–$C_{18}$ alcohol ethoxylate having 5–10 mol ethoxylate, and/or (3) a tristyrenephenol-ethoxylate having 8–30 mol ethoxylate, or its phosphate or salt thereof;

said composition further comprising a gelling agent, and wherein said composition is in the form of a gel and has a viscosity of 500 to 20,000 mPas.

37. A composition according to claim 36, wherein the concentration of the gelling agent is 0.1 to 10% by weight in relation to the volume of the composition.

38. The composition of claim 37 wherein said gelling agent is present in said composition at a concentration of 0.5 to 5% in relation to the volume of the composition.

* * * * *

UNITED STATES PATENT AND TRADEMARK OFFICE
CERTIFICATE OF CORRECTION

PATENT NO. : 6,071,857
DATED : June 6, 2000
INVENTOR(S) : Vogt et al.

It is certified that error appears in the above-identified patent and that said Letters Patent is hereby corrected as shown below:

<u>Title page, item 30,</u>
Line 1, should read: "Jun. 28, 1996 [EP] Europe.....................96810432.3"

<u>Claims, column 10,</u>
Insert the following:
"39. A liquid pesticidal composition, which is substantially free of water, comprising a hydrophobic pesticide or mixture of pesticides dissolved in an organic solvent and comprising as surfactants (1) a butanol-ethoxylate/propoxylate blockcopolymer having 12-30 mol ethoxylate and 16-48 mol propoxylate, in combination with (2) a branched $C_8$-$C_{18}$ alcohol ethoxylate having 5-10 mol ethoxylate, and/or (3) a tristyrenephenol-ethoxylate having 8-30 mol ethoxylate, or its phosphate or salt thereof; wherein said organic solvent is water miscible and selected from the group consisting of alcohols, glycols, N-methyl-2-pyrrolidone, tetramethylurea, gamma-butyrolactone, dimethylsulfoxide, N,N-dimethylacetamid, and dimethylformamide."

Signed and Sealed this

Twenty-fifth Day of September, 2001

Attest:

NICHOLAS P. GODICI
Attesting Officer          Acting Director of the United States Patent and Trademark Office